United States Patent
Routbort et al.

(10) Patent No.: US 8,057,652 B2
(45) Date of Patent: Nov. 15, 2011

(54) HIGH-TEMPERATURE POTENTIOMETRIC OXYGEN SENSOR WITH INTERNAL REFERENCE

(75) Inventors: Jules L. Routbort, Hinsdale, IL (US); Dileep Singh, Naperville, IL (US); Prabir K. Dutta, Worthington, OH (US); Ramamoorthy Ramasamy, North Royalton, OH (US); John V. Spirig, Columbus, OH (US); Sheikh Akbar, Hilliard, OH (US)

(73) Assignee: UChicago Argonne, LLC, Chicago, IL (US)

(*) Notice: Subject to any disclaimer, the term of this patent is extended or adjusted under 35 U.S.C. 154(b) by 858 days.

(21) Appl. No.: 11/228,064

(22) Filed: Sep. 16, 2005

(65) Prior Publication Data
US 2006/0213771 A1    Sep. 28, 2006

Related U.S. Application Data

(60) Provisional application No. 60/665,697, filed on Mar. 28, 2005.

(51) Int. Cl.
*G01N 27/407* (2006.01)

(52) U.S. Cl. .................................. 204/421; 204/424

(58) Field of Classification Search ................ 29/592.1; 204/400, 403, 435, 420–431; 205/775; 156/89.11–89.28
See application file for complete search history.

(56) References Cited

U.S. PATENT DOCUMENTS

| | | | | |
|---|---|---|---|---|
| 3,915,830 A | * | 10/1975 | Isenberg | 204/426 |
| 4,284,486 A | * | 8/1981 | Shinohara et al. | 204/424 |
| 4,502,939 A | | 3/1985 | Holfelder et al. | |
| 4,808,293 A | * | 2/1989 | Fukuda et al. | 204/410 |
| 5,169,513 A | * | 12/1992 | Mase et al. | 204/429 |
| 5,308,469 A | * | 5/1994 | Aldinger et al. | 204/426 |
| 5,360,528 A | | 11/1994 | Oh et al. | |
| 5,543,025 A | | 8/1996 | Garzon et al. | |
| 5,695,624 A | | 12/1997 | Garzon et al. | |
| 5,827,415 A | * | 10/1998 | Gur et al. | 204/426 |
| 6,196,049 B1 | * | 3/2001 | Schneider | 73/23.2 |
| 6,440,028 B2 | | 8/2002 | Kim et al. | |
| 2003/0029910 A1 | * | 2/2003 | Goretta et al. | 228/248.1 |

OTHER PUBLICATIONS

W.D. Emery, et al., Introduction to Ceramics, 2nd Edition, 1976, John F. Wiley & Sons publishers, p. 469.

* cited by examiner

*Primary Examiner* — Alex Noguerola
*Assistant Examiner* — Gurpreet Kaur
(74) *Attorney, Agent, or Firm* — Cherskov & Flaynik

(57) ABSTRACT

A compact oxygen sensor is provided, comprising a mixture of metal and metal oxide an enclosure containing said mixture, said enclosure capable of isolating said mixture from an environment external of said enclosure, and a first wire having a first end residing within the enclosure and having a second end exposed to the environment. Also provided is a method for the fabrication of an oxygen sensor, the method comprising confining a metal-metal oxide solid mixture to a container which consists of a single material permeable to oxygen ions, supplying an electrical conductor having a first end and a second end, whereby the first end resides inside the container as a reference $(PO_2)^{ref}$, and the second end resides outside the container in the atmosphere where oxygen partial pressure $(PO_2)^{ext}$ is to be measured, and sealing the container with additional single material such that grain boundary sliding occurs between grains of the single material and grains of the additional single material.

12 Claims, 8 Drawing Sheets

HIGH-TEMPERATURE POTENTIOMETRIC OXYGEN SENSOR WITH INTERNAL REFERENCE

This application claims the benefit of U.S. Provisional Application No. 60/665,697 filed on Mar. 28, 2005.

CONTRACTUAL ORIGIN OF INVENTION

The United States Government has rights in this invention pursuant to Contract No. W-31-109-ENG-38 between the U.S. Department of Energy and the University of Chicago, representing Argonne National Laboratory, and also pursuant to Award No. DE-FC26-03NT41615 between the U.S. Department of Energy and Ohio State University.

BACKGROUND OF THE INVENTION

1. Field of the Invention

This invention relates to an improved compact oxygen sensor and, more specifically, this invention relates to a method of making a high-temperature solid-state potentiometric oxygen sensor with an internal reference sealed by plastic joining.

2. Background of the Invention

Oxygen sensors are required to monitor oxygen levels in combustion and industrial processes. Typical oxygen sensors require a continuous supply of reference oxygen (usually air). Such sensors are expensive inasmuch as complex plumbing is required to route the reference gas to the sensor. As a result of the need for such plumbing, the locations of the sensors are also restricted and usually relegated to more mild locations within a process stream. For example, typical oxygen sensors are usually placed inside the flue of a combustion system and not in the actual combustion chamber. Indeed, temperatures approaching 1600° C. are often reached in such combustion chambers.

There are two types of oxygen sensors: amperiometric and potentiometric. Amperiometric sensors require a voltage source to function.

Potentiometric sensors require an external gas source. Moreover, additional plumbing is required to route said external gas to an interior region of the sensor. Potentiometric sensors contain internal references which require glass seals, metal housings, and similar materials which are not robust and not suited to thermal cycling. As such, typical potentiometric sensors are restricted to low temperature operations.

Past efforts in fabricating autonomous sensors (i.e., not requiring external plumbing) have had only partial success. For example, U.S. Pat. No. 5,827,415 awarded to Gur et al. on Oct. 27, 1998, utilizes a solid electrolyte slab having a first side covered with a sensing electrode and a second side containing a metal-metal oxide reference electrode. The metal-metal oxide electrode is isolated from the environment using glass seals to keep out oxygen. However, glass seals limit the operational temperature and become brittle with temperature cycling.

U.S. Pat. No. 3,915,830 awarded to Isenberg on Oct. 28, 1975 discloses a reference medium encapsulated by solid electrolyte, the later of which is sputtered, plated or otherwise deposited onto the medium. A lead wire from the reference medium is routed to outside of the resulting construct and sealed with glass. As mentioned supra, glass tends to become brittle during temperature cycling and limits the operational temperature.

U.S. Pat. No. 6,440,028 awarded to Kim, et al. on Aug. 27, 2002 discloses a manual valve of a hydraulic pressure control system for automatic transmission. The invention requires an atmospheric reference and a voltage source. Numerous different materials are involved in its manufacture, several of which restrict thermal cycling applications.

U.S. Pat. No. 5,360,528 awarded to Oh, et al. on Nov. 1, 1994 discloses a wide range oxygen sensor. However, the applicable current is limited, many materials are required for manufacture, and there is restricted range of thermal cycling and temperature operation.

U.S. Pat. No. 5,543,025 awarded to Garzon, et al. on Aug. 6, 1996 and U.S. Pat. No. 5,695,624 awarded to Garzon, et al. on Dec. 9, 1997 both disclose a solid state oxygen sensor with a yttria-doped zirconia as an electrolyte. Both inventions require glass seals, which limit operational temperature and thermal cycling due to the glass' tendency to become brittle.

U.S. Pat. No. 4,502,939 awarded to Holfelder, et al. on Mar. 5, 1985 discloses an electrochemical oxygen sensor, particularly for analysis of combustion cases from internal combustion engines. It requires metal housing, limits operational temperature and limits thermal cycling.

Thin film sensors, as in most of the patents described supra, are no longer available because they are expensive to make and not robust.

A need exists in the art for a high-temperature oxygen sensor that is compact and inexpensive, and a method for producing such a sensor. The sensor should obviate the need for reference oxygen plumbing and therefore the need for oxygen gas as reference $pO_2$. The sensor should also be robust in a myriad of environments, and particularly in high-temperature and fluctuating temperature situations such as effluent streams, industrial waste streams, combustion streams, process streams, $NO_x$ traps, and turbines. Such a robust nature would be the result of a fabrication process utilizing plastic deformation to seal or otherwise isolate internal reference material from the harsh environments.

SUMMARY OF INVENTION

An object of the present invention is to provide an oxygen sensor and a method for fabricating an oxygen sensor that overcomes many of the disadvantages of the prior art.

Another object of the present invention is to provide a low cost miniaturized oxygen sensor that operates in extreme environments. A feature of the invention is that the sensor is compact and operates between 450° C. and 800° C., with the range of temperature extendable to 1600° C. An advantage of the invention is that spatial maps of oxygen content of industrial and combustion processes can be monitored for fuel utilization efficiencies, by using a plurality of sensors.

Yet another object of the present invention is to provide a method for fabricating a low-cost oxygen sensor. A feature of the invention is a sensor housing comprising solely homogenous material (such that the housing is uniform through out its bulk) One such material is an evenly mixed oxygen conductor such as tetragonal phase yttrium-stabilized zirconium. An advantage of the invention is that the sensor material allows for one-step fabricating whereby heat and pressure are simultaneously applied to develop a compact, high temperature resistant construct via plastic deformation.

Briefly, the invention provides an oxygen sensor comprising a mixture of metal and metal oxide; an enclosure containing said mixture, said enclosure capable of isolating said mixture from an environment external of said enclosure, and a wire having a first end residing within the enclosure and having a second end exposed to the environment.

The invention also provides a method for the fabrication of an oxygen sensor, the method comprising confining a metal-metal oxide solid mixture to a container or housing which consists of a single material permeable to oxygen ions; supplying an electrical conductor having a first end and a second end, whereby the first end is at the reference oxygen partial pressure determined by the decomposition of the metal oxide at the operational temperature and the second end resides outside the container exposed to the oxygen atmosphere to be measured. Sealing the container is accomplished by application of pressure and temperature that results in grain boundary sliding and the accompanying grain rotation amongst particles comprising the material, resulting in a pore-free, gas-tight seal.

BRIEF DESCRIPTION OF DRAWING

The invention together with the above and other objects and advantages will be best understood from the following detailed description of the preferred embodiment of the invention shown in the accompanying drawing, wherein.

DETAILED DESCRIPTION OF THE INVENTION

Figure 1:
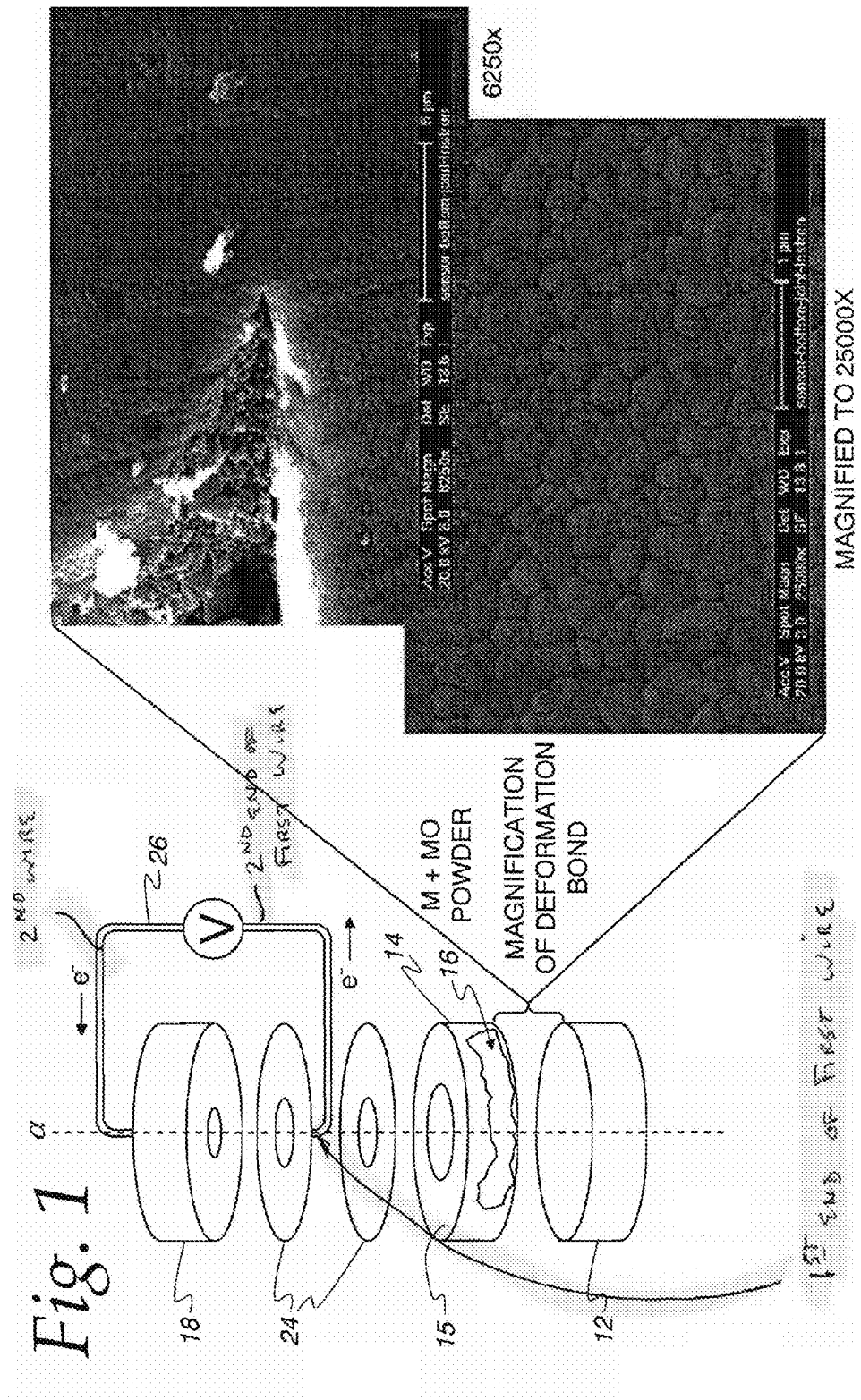
FIG. 1 is an exploded view of the sensor, in accordance with features of the present invention.

The instant invention provides a low cost, potentiometric compact oxygen sensor and a method for fabricating the oxygen sensor. The sensor has exceptional utility in that is can be used in high temperature and otherwise harsh environments. For example, sensors constructed with the invented method are operational in gas phases, and also in molten fluids, at temperatures above 650° C. Generally, as long as the housing of the invented sensor is maintained at a temperature below which constituents of the housing become mixed ion-conductors, the sensor is operational. So, in the case of a housing containing zirconium, the sensor is operational as high as 1600° C.

Salient features of the invention include the use of yttria-stabilized zirconium (YSZ) as sensor housing material and oxygen ion conductor and a metal-metal oxide mixture as a means for providing oxygen reference values. (Other ceramic oxygen ion conductors such as cerium oxide may also be used in place of YSZ.) As such, the sensors can reside directly in combustion chambers to offer fast response (compared to less robust sensors which must be placed downstream in cooler areas, such as the flue because of the required plumbing for the reference gas and the limits on sensor operation temperatures).

The fabrication protocol of the sensor incorporates the use of plastic deformation accompanied by atomic diffusion. Seamless joining of solid objects occurs via diffusion of particles, not by reactive processes between particles. The resulting construct which is produced has a seamless pore-free topography. Plastic deformation occurs between the objects themselves and/or a joint compound comprised of the same material as the objects to be joined. The construction of a sensor housing using single-phase material (i.e., homogenously dispersed material) throughout the bulk of the housing eliminates the impedance seen when dissimilar, conductivity-altering intermediate bonding materials are utilized. Also, no surface preparation of component surfaces is required to assure seamless bonding. Otherwise, the use of sealants could lower the operating temperature of the sensor, result in failure of the sensor, or modify physical (electrical) properties of the objects comprising the sensor.

As a result of the seamless construction of the sensor, extremely accurate differentials in oxygen partial pressures can be determined up to 1600° C. The accuracy of the sensor depends on the accuracy of the potential between the internal reference and the sensor's environment. Based on the noise characteristics of the measurement, differences in oxygen concentration of 0.1% can be readily measured.

Generally, the minimum partial pressure that can be measured will depend on several factors, including the operating temperature at the metal-metal oxide reference. At typical operating temperatures of approximately 700° C. the minimum partial pressure that can be measured is about $1\times10^{-10}$ atmospheres (atm), i.e., the pressure at which electronic conductivity in YSZ competes with ionic conductivity.

Fabrication Detail of Sensor Housing

Plastic deformation is a diffusion-controlled process whereby grain boundaries slide by each other and rotate to accommodate the small plastic strain imposed by the applied stress at the joining temperatures. By its nature, boundary sliding occurs only if grains maintain their physical dimension and integrity so as to allow the grains to slide and intermingle with respect to grains of contacting structures. Plastic Forming (PF) is a hot working manufacturing technique. PF is used to produce complex, high-strength components from a single manufacturing operation.

In the instant fabrication process, sensor housing components are assembled and then subjected to heat and pressure so that the material (and the particles comprising that material) of one component disperses and intermingles with the material of another component to form a seamless, gas-tight unitary structure. Details of the plastic joining process are found in U.S. patent application Ser. No. 09/924,571, filed on Aug 7, 2001 and incorporated herein by reference. That application was published on Feb. 13, 2003 as publication number US-2003-0029910-A1.

The invention provides a method for sealing or encapsulating the internal reference material within a compartment of yttria-stabilized zirconium (YSZ) by plastic deformation. An exploded view of the sensor's components is provided in FIG. 1. This view is provided as an illustration only and should not relegate the claims herein to specific configurations shown in FIG. 1.

A base plate 12 of YSZ is provided of desired size and shape; in this exemplary case, the plate resembles a disk. A hollow cylinder 14 is placed on top of the plate to form a cylinder having a closed bottom. (To expedite high volume production processes, a cylinder closed at one end can be a starting component.)

Within the closed bottom cylinder is positioned an amount of metal-metal oxide mixture 16.

Figure 2:
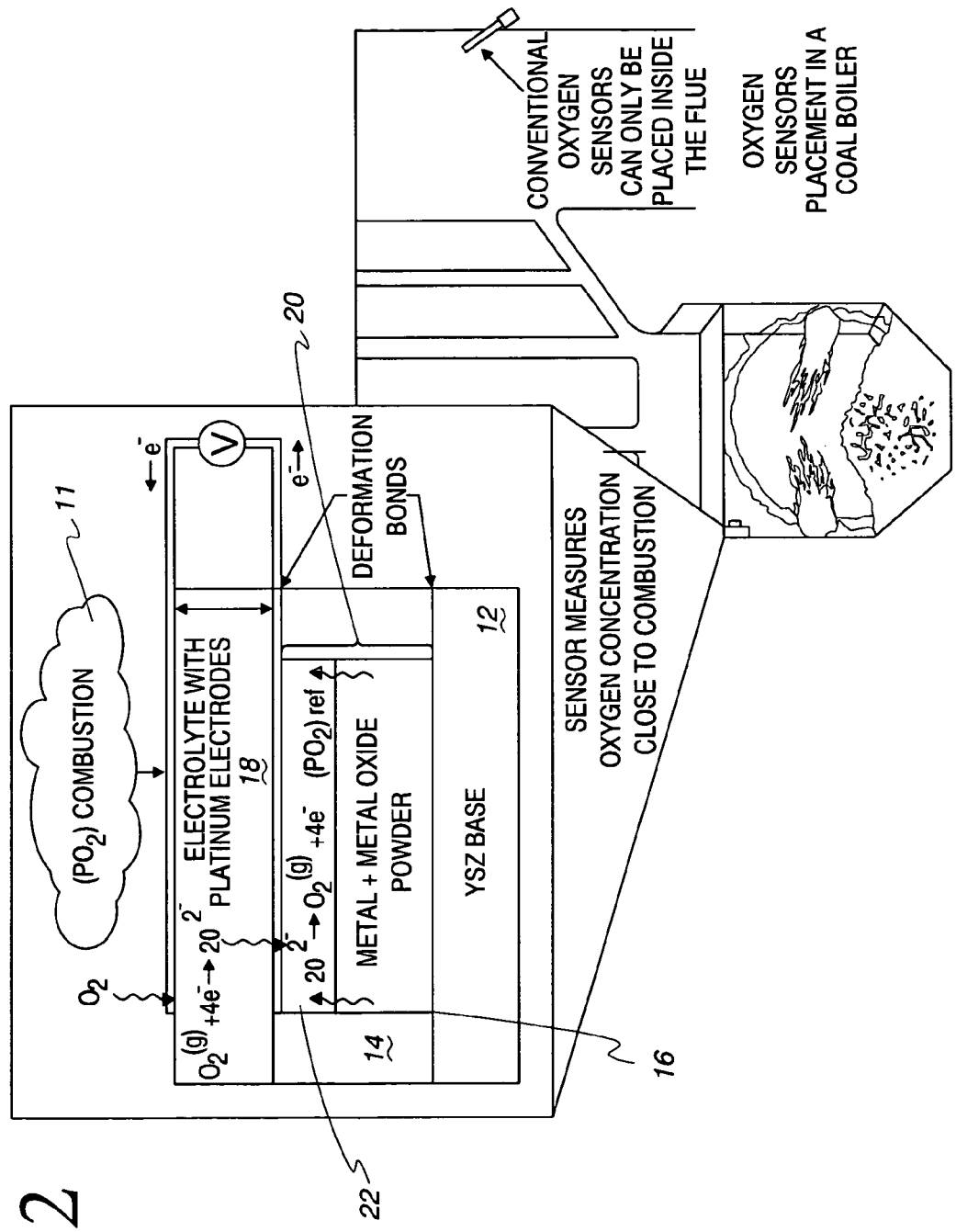
FIG. 2 is an elevated schematic view of the sensor.
Figure 3:
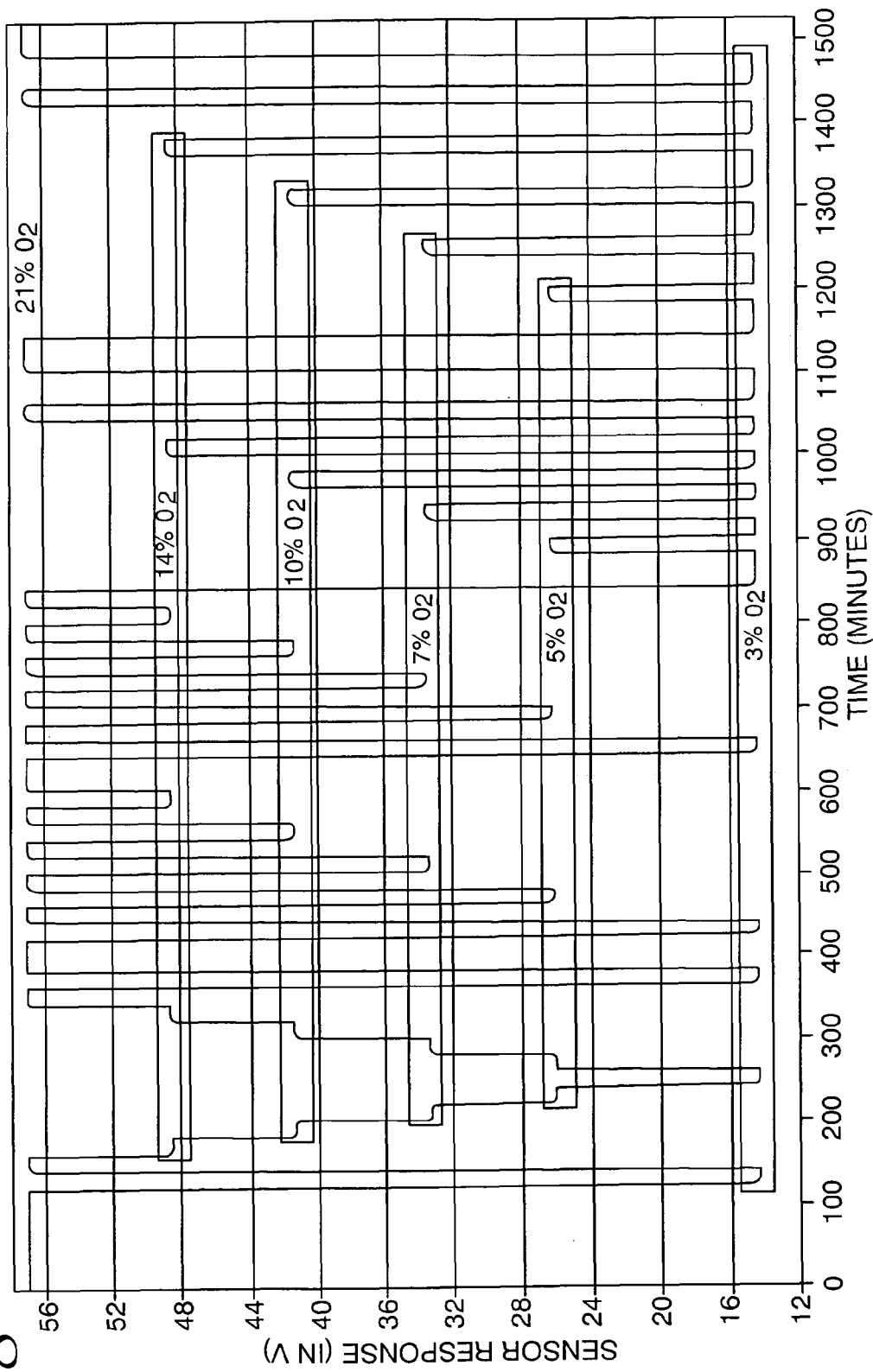
FIG. 3 is a graph showing the sensitivity of the invented sensor operating at 700° C. in a myriad of oxygen concentrations.
Figure 4A:
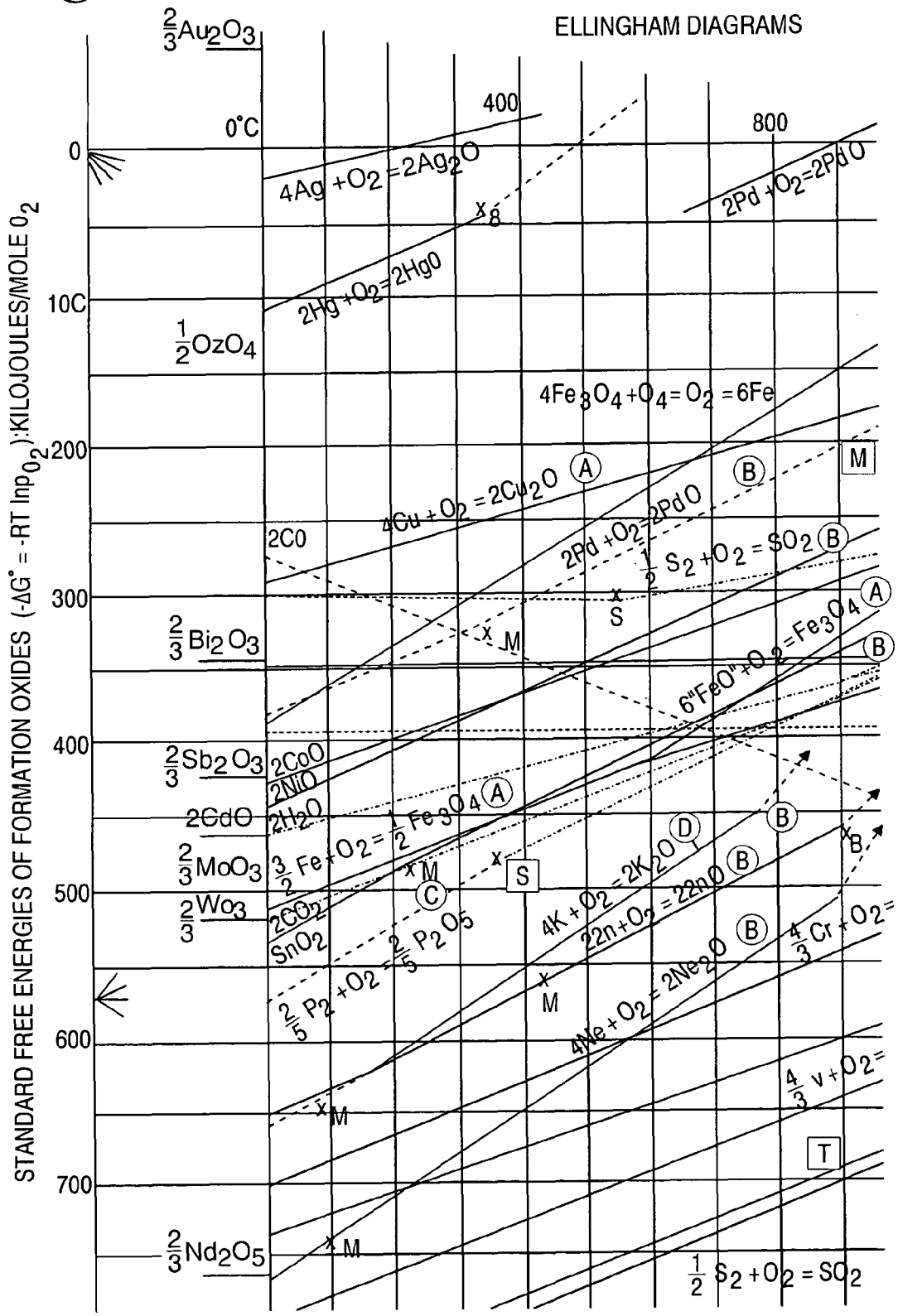
FIG. 4 is an Ellingham Diagram depicting exemplary metal-metal oxide candidates as means for establishing oxygen reference values, in accordance with features of the present invention.
Figure 4B:
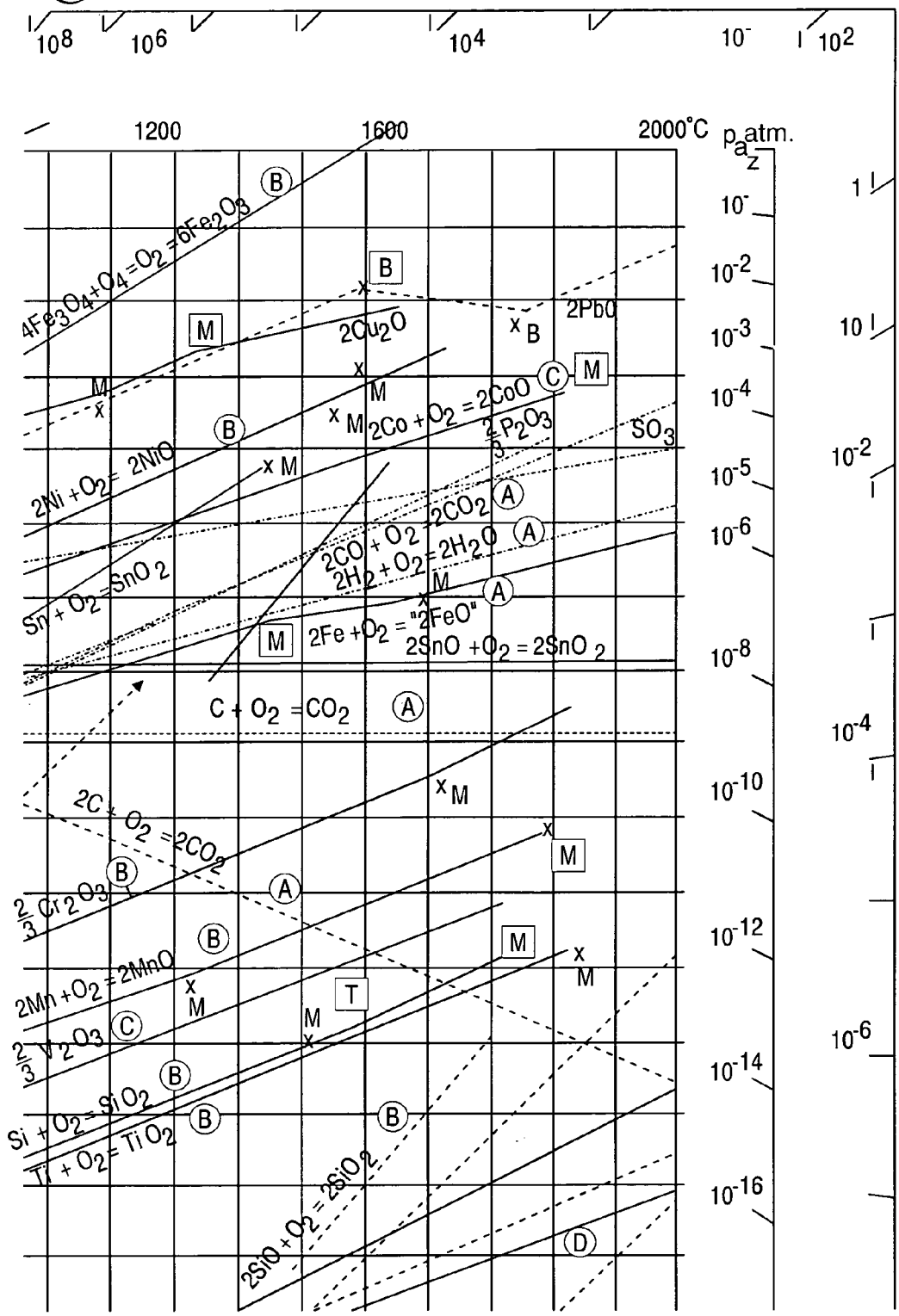
Figure 4C:
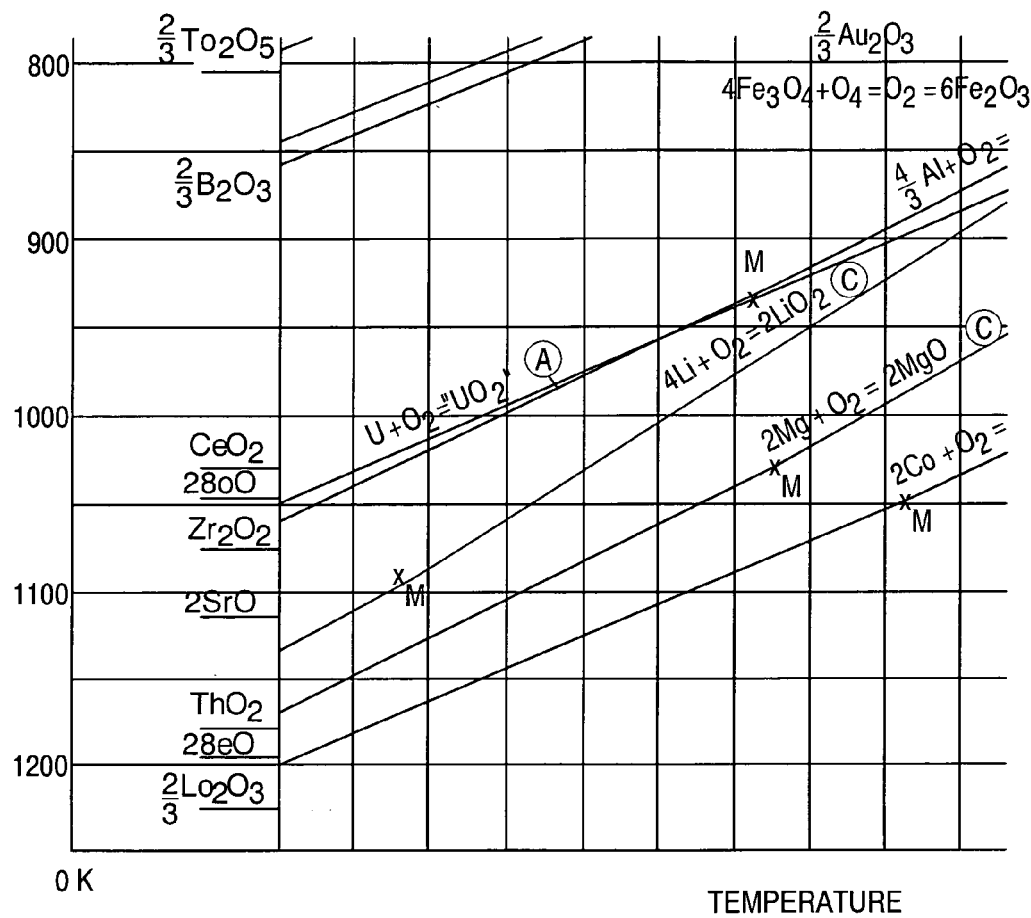
Figure 4D:
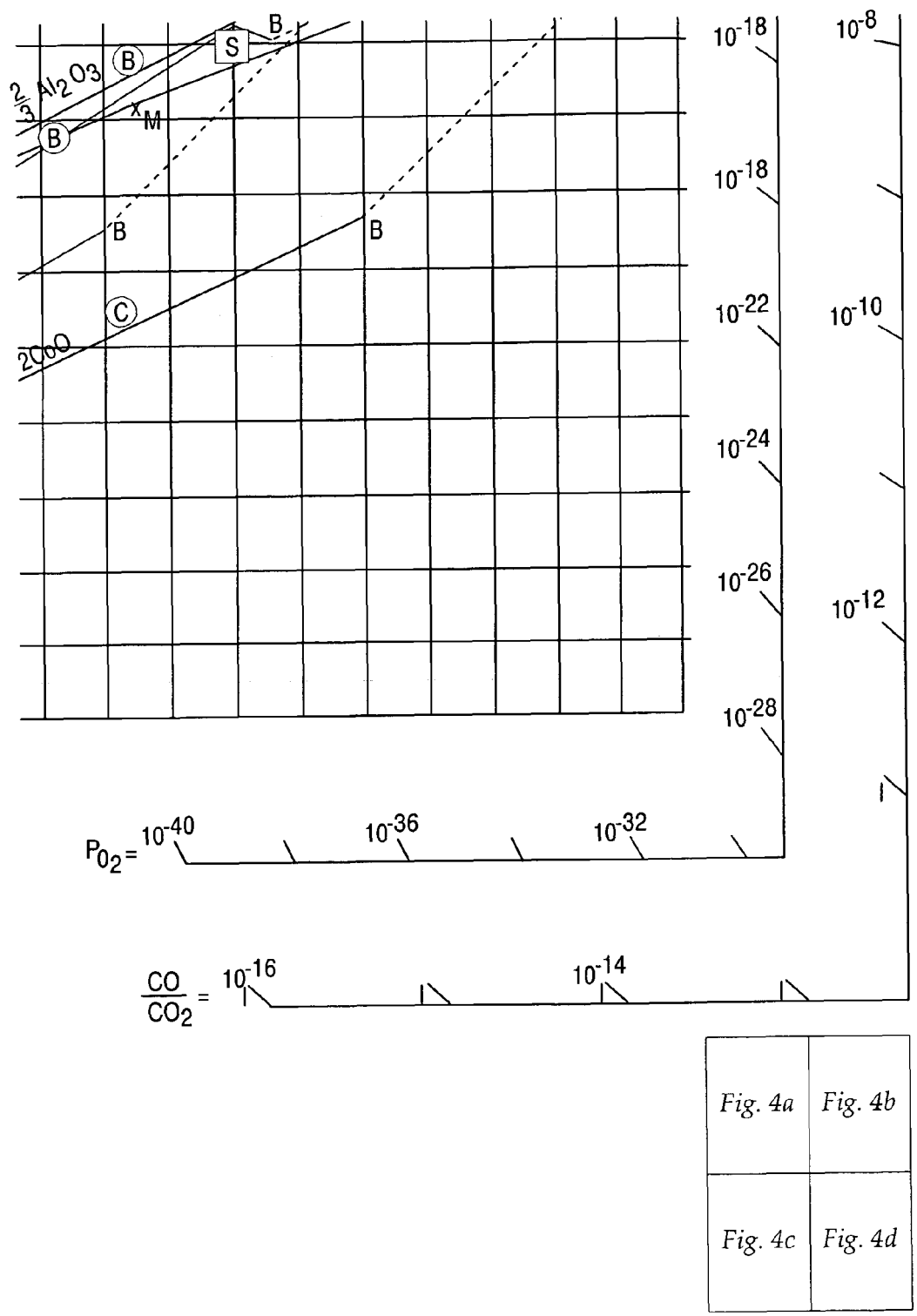
Figure 5:
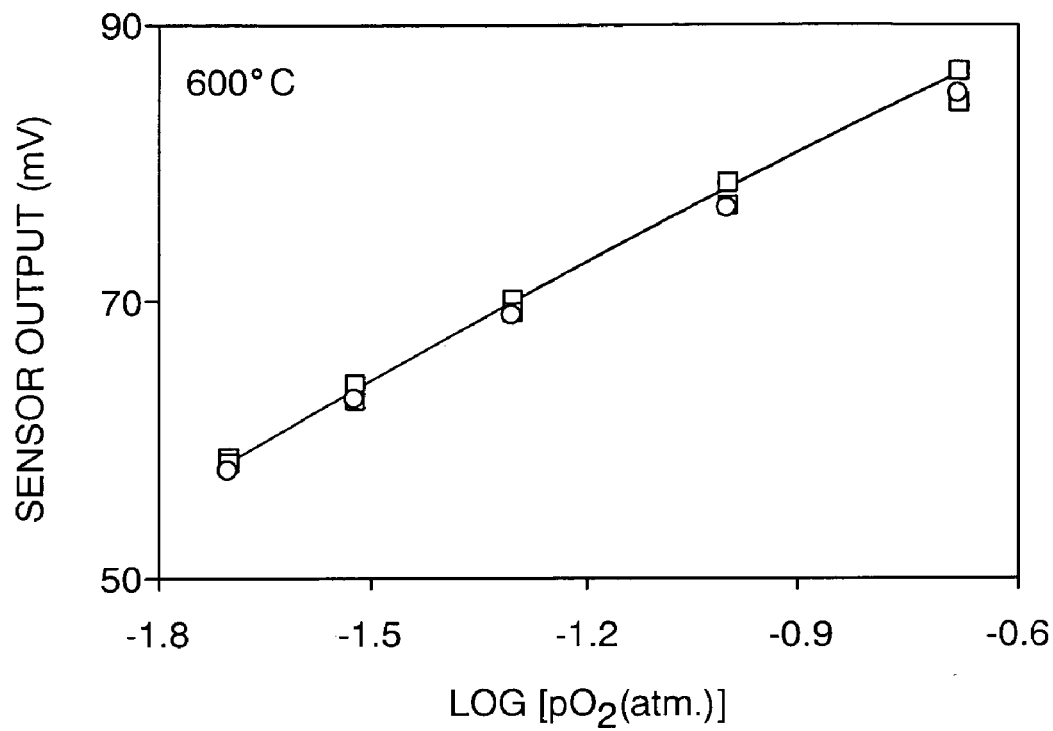
FIG. 5 is a graph showing voltage potential generated by the invented sensor at various oxygen concentrations, in accordance with features of the present invention.

A cap or cover 18 is positioned on an upwardly facing surface 15 of the cylinder 14 so as to define an internal reaction chamber 20, including a head space 22, so depicted in FIG. 2. The metal-metal oxide mixture 16 resides in the chamber 20 and below the head space 22. This internal reaction chamber 20 is essentially a self-contained reference oxygen chamber. The head space 22 is needed for gas evolution and to avoid reaction of a conduction wire 26 with the metal and metal-oxide mixture. As such, the head space 22 is a confined volume of gas that serves as a means for separating the conductor wire 26 from the metal-metal oxide mixture. The head space serves as a controlled environment and is hermetically sealed from the external environment of the sensor so as to prevent fluid communication with the external environment contacting the exterior 11 of the sensor.

The conductor wire 26 or other means for measuring current is positioned between the cap 18 and cylinder 14. The wire serves to measure electron flow as a result of the difference in oxygen partial pressures between the chamber 20 and the exterior 11 of the sensor during sensor operation.

Also positioned intermediate the cap 18 and surface 15 is YSZ tape or film 24. This deformable tape serves to eliminate any gaps which exist between the abutting cap and cylinder caused by the wire positioned therebetween. In this exemplar, YSZ tape 24 is applied to each of the cap 18 and the surface 15 to facilitate formation of a non-porous seal. Other means of sealing could include using slurries or pastes of yttria-stabilized zirconia and various glasses.

Once the above-mentioned sensor elements are assembled and positioned, the construct is simultaneously heated and subjected to pressure, the latter along the longitudinal axis of the sensor (i.e., uniaxial stress is applied), the axis designated as a in FIG. 1. Generally, temperatures of between 1200° C. and 1400° C. and pressures between 5 mega Pascals (MPa) and 100 MPa are employed to facilitate the grain boundary sliding necessary to effect the formation of seamless joints. The amount of heat applied is inversely proportional to the amount of pressure applied, so that less heat is necessary if more pressure is applied, and vice versa. More extreme heat and pressure applications are used to increase fabrication rates of the sensors. Sensor fabrication is generally done in argon gas or air depending on the metal-metal oxide mixture used. Fabrication in nonoxidizing or otherwise inert environments viz the metal oxide may be preferable, so as to minimize the possibility of capturing oxygen within the head space or other portions of the interior of the sensor.

When a suitable stress (pressure) is applied at a suitable temperature to perform the bonding, the pieces undergo plastic deformation, that is, permanent deformation, via grain boundary sliding. The material is not elastic, but plastic, meaning that the length of the construct will change. As such, if the complete construct is 1 cm in length, it might end up being 10 percent shorter (i.e. 0.9 cm) inasmuch as the deformation is compressive. In most cases, total compression strains are less than 10 percent.

A myriad of oxygen ion conductor materials are suitable as constituents of the housing of the sensor. Exemplary materials include, but are not limited to zirconium oxide, yttria-stablized zirconia, cerium oxide, and zirconium oxide doped with oxides which stabilize zirconium as a tetrahedral lattice structure. Suitable dopants include, but are not limited to barium oxide, calcium oxide, hafnium oxide, magnesium oxide, or combinations thereof.

Metal-Metal Oxide Selection Detail

The type of mixture inserted into the bottom of the cylinder is determined based on the oxygen concentrations to be measured and the temperatures to which the sensor is to be subjected. As such, widely disseminated references, such as the Ellingham Diagram (see FIG. 4) are utilized to determine the appropriate metal-metal oxide mixture, once sensor environs are determined.

The Ellingham diagram shown in FIG. 4 is for metals reacting to form oxides (similar diagrams can also be drawn for metals reacting with sulfur, chlorine, etc., but the oxide form of the diagram is most common). The sensor relies on the Ellingham diagram to determine the partial pressure of oxygen that is in equilibrium with a metal oxide at a given temperature. As such, the stability of the oxide is a function of temperature. Reactions closer to the top of the diagram are the most "noble" metals (for example, gold and platinum), and their oxides are unstable and easily reduced. As one moves down toward the bottom of the diagram, the metals become progressively more reactive and their oxides become harder to reduce.

A myriad of metal-metal oxide mixtures can be employed as internal reference $(PO_2)_{ref}$ markers for the sensor. Stoichiometric and nonstoichiometric metal oxides are suitable candidates. Nonstoichiometric takes on its typical meaning herein, which is to say that generally, in a solid chemical compound comprising the metal oxide, the numbers of component atoms are not in a simple numeric ratio; specifically in nonstoichiometric mixtures, the oxygen atoms are deficient. Suitable metals and their metal oxides include, but are not limited to, nickel, palladium, iron, zinc, cobalt, tin, lead, copper, ruthenium, vanadium, manganese, chromium, and rhenium. The metal-metal oxide mixture chosen for the sensor depends on the target partial pressures to be measured and the sensor operating temperatures.

A preferred embodiment of the sensing element is a closed-end device made from ceramic zirconium oxide stabilized with an oxide of yttrium. Platinum coatings on the inside and outside serve as both a catalyst and as electrodes. At temperatures above 450° C., the oxygen molecules that come into contact with the platinum electrodes on the sensor become ionic. As long as the oxygen partial pressures on either side of the cell are equal, the driving force is zero and the movement of the ions is random, resulting in no potential being generated. However, if gases have different oxygen partial pressures on either side of the cell, a voltage is developed. The magnitude of the voltage is a logarithmic function of the ratio of the two oxygen partial pressures, and the temperature as dictated by the Nernst equation as set forth infra.

If the oxygen partial pressure of one gas is known (as would be the case using the Ellingham diagram), the voltage produced by the cell indicates the oxygen content of the gas stream in which the sensor is immersed. The sensor's internal reference oxygen atmosphere, produced when the metal-metal oxide powder inside is heated, replaces a conventional external reference air supply and plumbing. The process temperature can be continuously monitored by an inexpensive thermocouple. The oxygen content of the target fluid is determined from the Nernst equation $E=(RT/4F)\ln[(PO_2^{ext}/PO_2^{int})]$, where R and F are constants, T is the absolute temperature, and $PO_2^{ext}$ and $PO_2^{int}$ are the oxygen partial pressures on either side of the cell.

Preferably, to assure accuracy and reproducibility of the sensor, temperatures will be well-controlled by attaching the sensor package to a local heater, inasmuch as the enclosure is capable of conducting heat from the environment to the mixture. Also, the temperature of the target stream generally should be below that which would render the housing material a mixed ion conductor. The dynamic range of the sensor is from 1 ppm $PO_2$ to 1 atm $PO_2$.

While the invention has been described with reference to details of the illustrated embodiment, these details are not intended to limit the scope of the invention as defined in the appended claims. For example, temperatures also can be determined with the sensor. In such a scenario, given a fixed partial pressure of oxygen, voltage changes indicate temperature changes.

The invention claimed is:

1. A method for the fabrication of a potentiometric oxygen sensor, the method comprising:

a. confining a metal-metal oxide solid mixture to a container having a cap and a base wherein the said container consists of a single material that conducts oxygen ions;
b. supplying a first wire having a first end that resides inside the container at a reference oxygen partial pressure, a second end which resides outside the container and a second wire that resides outside the container, wherein the first wire is separated from the mixture via a head space positioned above the mixture; and
c. sealing the container by deforming additional said single material to surround the first wire and the single material via plastic deformation with grain boundary sliding imposed by applied stress such that a pore-free, gas tight joint exists between the single material and the additional said single material so as to prevent fluid communication between the mixture and the external environment contacting the exterior of the sensor, wherein the additional said single material is positioned intermediate the cap and the base of the container.

2. The method as recited in claim 1 wherein the step of sealing the container further comprises subjecting the single material and the additional single material to a temperature sufficient to cause plastic deformation to occur between the single material and the additional single material.

3. The method as recited in claim 1 wherein the step of sealing the container further comprises subjecting the single material and the additional single material to a temperature and pressure sufficient to cause plastic deformation to occur between the single material and the additional single material.

4. The method as recited in claim 2 wherein the temperature is selected from between 1200° C. and 1400° C.

5. The method as recited in claim 3 wherein the pressure is applied in a direction generally perpendicular to the plane formed by abutting surfaces of the single material and additional single material.

6. The method as recited in claim 3 wherein the pressure is selected from between 5 MPa and 100 MPa.

7. The method as recited in claim 3 wherein the pressure applied to the single material and additional single material results in strains of less than 10%.

8. The method as recited in claim 1 wherein the solid mixture is a powder.

9. The method as recited in claim 1 wherein the additional said single material is applied as a slurry or paste to facilitate formation of a nonporous seal.

10. The method as recited in claim 1 wherein the additional said single material is applied as a tape.

11. The method as recited in claim 1 wherein the single material and additional single material comprise grains and the grains maintain their physical dimensions.

12. A sensor fabricated by the method recited in claim 1.

\* \* \* \* \*